US006758860B1

(12) United States Patent
Penn et al.

(10) Patent No.: US 6,758,860 B1
(45) Date of Patent: *Jul. 6, 2004

(54) EXPANDABLE STENT AND METHOD FOR DELIVERY OF SAME

(75) Inventors: Ian M. Penn, Vancouver (CA); Donald R. Ricci, Vancouver (CA)

(73) Assignee: Envysio Medical Devices ULC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/672,768

(22) Filed: Sep. 29, 2000

Related U.S. Application Data

(63) Continuation of application No. 09/142,509, filed as application No. PCT/CA97/00152 on Mar. 5, 1997, now Pat. No. 6,183,506.

(30) Foreign Application Priority Data

| Mar. 5, 1996 | (CA) | 2171047 |
|---|---|---|
| May 3, 1996 | (CA) | 2175722 |
| Sep. 17, 1996 | (CA) | 2185740 |
| Dec. 10, 1996 | (CA) | 2192520 |

(51) Int. Cl.[7] .................................................. A61F 2/06
(52) U.S. Cl. ..................................... 623/1.16; 623/1.15
(58) Field of Search .............................. 623/1.1, 1.11, 623/1.12, 1.15

(56) References Cited

U.S. PATENT DOCUMENTS

| 3,657,774 A | 4/1972 | Reynolds ................. 24/73 CF |
| 3,993,078 A | 11/1976 | Bergentz et al. ........ 128/334 R |
| 4,503,569 A | 3/1985 | Dotter ............................ 3/1.4 |
| 4,553,545 A | 11/1985 | Maass et al. ............... 128/341 |
| 4,580,568 A | 4/1986 | Gianturco .................. 128/345 |
| 4,655,771 A | 4/1987 | Wallsten ....................... 623/1 |
| 4,681,110 A | 7/1987 | Wiktor ....................... 128/343 |
| 4,733,665 A | 3/1988 | Palmaz ....................... 128/343 |
| 4,739,762 A | 4/1988 | Palmaz ....................... 128/343 |
| 4,762,128 A | 8/1988 | Rosenbluth ................. 128/343 |
| 4,768,507 A | 9/1988 | Fischell et al. ......... 128/303 R |
| 4,795,458 A | 1/1989 | Regan ........................... 623/1 |
| 4,800,882 A | 1/1989 | Gianturco .................. 128/343 |
| 4,830,003 A | 5/1989 | Wolff et al. ................ 128/343 |
| 4,856,516 A | 8/1989 | Hillstead .................... 128/343 |
| 4,878,906 A | 11/1989 | Lindemann et al. ........... 623/1 |

(List continued on next page.)

FOREIGN PATENT DOCUMENTS

| CA | 1239755 | 8/1988 | ............. A61F/2/00 |
| CA | 1245527 | 11/1988 | .......... A61M/29/00 |

(List continued on next page.)

OTHER PUBLICATIONS

Lawrence et al., "Percutaneous Endovascular Graft: Experimental Evaluation," 1987 RSNA Annual Meeting, Radiology, vol. 163, pp. 357–360 (May 1987).

(List continued on next page.)

Primary Examiner—Corrine McDermott
Assistant Examiner—William Matthews
(74) Attorney, Agent, or Firm—Katten Muchin Zavis Rosenman

(57) ABSTRACT

An expandable stent having a proximal end and a distal end in communication with one another, and a tubular wall disposed between the proximal end and the distal end. The tubular wall has a longitudinal axis and a porous surface defined by a plurality of intersecting members comprising a series of longitudinal struts disposed substantially parallel to the longitudinal axis of the stent. Each longitudinal strut in the series comprises flexure members for substantially complementary extension and compression of a diametrically opposed pair of the longitudinal struts upon flexure of the stent. The flexure members may comprise first and second curved sections which are of a different size. At least one of the curved sections may comprise an arc of greater than about 180°.

22 Claims, 13 Drawing Sheets

U.S. PATENT DOCUMENTS

| | | | | |
|---|---|---|---|---|
| 4,886,062 A | 12/1989 | Wiktor | | 128/343 |
| 4,907,336 A | 3/1990 | Gianturco | | 29/515 |
| 4,954,126 A | 9/1990 | Wallstén | | 600/36 |
| 4,969,458 A | 11/1990 | Wiktor | | 606/194 |
| 4,994,071 A | 2/1991 | MacGregor | | 606/194 |
| 5,019,085 A | 5/1991 | Hillstead | | 606/108 |
| 5,035,706 A | 7/1991 | Giantureo et al. | | 606/198 |
| 5,037,392 A | 8/1991 | Hillstead | | 604/96 |
| 5,041,126 A | * 8/1991 | Gianturco | | 623/1.15 |
| 5,061,275 A | 10/1991 | Wallstén et al. | | 623/1 |
| 5,102,417 A | 4/1992 | Palmaz | | 606/195 |
| 5,104,404 A | 4/1992 | Wolff | | 623/1 |
| 5,108,417 A | 4/1992 | Sawyer | | 606/198 |
| 5,116,365 A | 5/1992 | Hillstead | | 623/1 |
| 5,133,732 A | 7/1992 | Wiktor | | 606/195 |
| 5,135,536 A | 8/1992 | Hillstead | | 606/195 |
| 5,139,480 A | 8/1992 | Hickle et al. | | 604/8 |
| 5,147,385 A | 9/1992 | Beck et al. | | 623/1 |
| 5,161,547 A | 11/1992 | Tower | | 128/898 |
| 5,192,307 A | 3/1993 | Wall | | 623/1 |
| 5,195,984 A | 3/1993 | Schatz | | 606/195 |
| 5,197,987 A | 3/1993 | Koch et al. | | 623/20 |
| 5,201,901 A | 4/1993 | Harada et al. | | 606/198 |
| 5,266,073 A | 11/1993 | Wall | | 623/1 |
| 5,269,802 A | 12/1993 | Garber | | 606/191 |
| 5,282,823 A | 2/1994 | Schwartz et al. | | 606/198 |
| 5,282,824 A | 2/1994 | Gianturco | | 606/198 |
| 5,290,305 A | 3/1994 | Inoue | | 606/191 |
| 5,292,331 A | 3/1994 | Boneau | | 606/198 |
| 5,314,472 A | 5/1994 | Fontaine | | 623/12 |
| 5,316,023 A | 5/1994 | Palmaz et al. | | 128/898 |
| 5,342,387 A | 8/1994 | Summers | | 606/198 |
| 5,383,892 A | 1/1995 | Cardon et al. | | 606/198 |
| 5,395,390 A | 3/1995 | Simon et al. | | 606/198 |
| 5,405,377 A | 4/1995 | Cragg | | 623/1 |
| 5,421,955 A | 6/1995 | Lau et al. | | 216/48 |
| 5,443,498 A | 8/1995 | Fontaine | | 623/1 |
| 5,443,500 A | 8/1995 | Sigwart | | 623/1 |
| 5,449,373 A | 9/1995 | Pinchasik | | 606/198 |
| 5,458,615 A | 10/1995 | Klemm et al. | | 606/198 |
| 5,496,365 A | 3/1996 | Sgro | | 623/1 |
| 5,507,767 A | 4/1996 | Maeda et al. | | 606/198 |
| 5,507,771 A | 4/1996 | Gianturco | | 606/198 |
| 5,514,154 A | 5/1996 | Lau et al. | | 606/195 |
| 5,522,880 A | 6/1996 | Barone et al. | | 623/1 |
| 5,527,354 A | 6/1996 | Fontaine et al. | | 623/1 |
| 5,540,712 A | 7/1996 | Kleshinski et al. | | 606/198 |
| 5,569,295 A | 10/1996 | Lam | | 606/198 |
| 5,575,771 A | 11/1996 | Walinsky | | 604/96 |
| 5,575,817 A | 11/1996 | Martin | | 623/1 |
| 5,591,197 A | 1/1997 | Orth et al. | | 606/194 |
| 5,603,721 A | 2/1997 | Lau et al. | | 606/195 |
| 5,607,442 A | 3/1997 | Fischell et al. | | 606/191 |
| 5,623,771 A | 4/1997 | Winheim | | 34/585 |
| 5,628,787 A | * 5/1997 | Mayer | | 623/1.15 |
| 5,634,941 A | 6/1997 | Winston et al. | | 623/1 |
| 5,639,278 A | 6/1997 | Dereume et al. | | 623/1 |
| 5,643,312 A | 7/1997 | Fischell et al. | | 606/198 |
| 5,643,340 A | 7/1997 | Nunokawa | | 623/1 |
| 5,653,743 A | 8/1997 | Martin | | 623/1 |
| 5,674,278 A | 10/1997 | Boneau | | 623/1 |
| 5,676,696 A | 10/1997 | Marcade | | 623/1 |
| 5,676,697 A | 10/1997 | McDonald | | 623/1 |
| 5,693,086 A | 12/1997 | Goicoechea et al. | | 623/1 |
| 5,697,971 A | 12/1997 | Fischell et al. | | 623/1 |
| 5,709,712 A | 1/1998 | Paul et al. | | 607/27 |
| 5,733,303 A | 3/1998 | Israel et al. | | 606/198 |
| 5,755,734 A | 5/1998 | Richter et al. | | 606/194 |
| 5,755,735 A | 5/1998 | Richter et al. | | 606/194 |
| 5,755,771 A | * 5/1998 | Penn | | 623/1.15 |
| 5,776,161 A | 7/1998 | Globerman | | 606/194 |
| 5,807,404 A | 9/1998 | Richter | | 623/1 |
| 5,824,040 A | 10/1998 | Cox et al. | | 623/1 |
| 5,827,320 A | 10/1998 | Richter et al. | | 606/194 |
| 5,836,964 A | 11/1998 | Richter et al. | | 606/194 |
| 5,836,966 A | 11/1998 | St. Germain | | 606/198 |
| 5,868,783 A | 2/1999 | Tower | | 623/1 |
| 5,879,370 A | 3/1999 | Fischell et al. | | 606/198 |
| 5,902,332 A | 5/1999 | Schatz | | 623/1 |
| 5,906,640 A | 5/1999 | Penn et al. | | 623/1 |
| 5,906,759 A | 5/1999 | Richter | | 219/121.63 |
| 5,911,754 A | 6/1999 | Kanesaka | | 623/1 |
| 5,913,895 A | 6/1999 | Burpee et al. | | 623/1 |
| 5,922,005 A | 7/1999 | Richter et al. | | 606/192 |
| 5,931,866 A | 8/1999 | Frantzen | | 623/1 |
| 5,964,770 A | 10/1999 | Flomenblit et al. | | 606/78 |
| 5,964,798 A | 10/1999 | Imran | | 623/12 |
| 5,980,552 A | 11/1999 | Pinchasik et al. | | 606/198 |
| 5,997,703 A | 12/1999 | Richter | | 204/297 |
| 6,017,362 A | * 1/2000 | Lau | | 623/1.2 |
| 6,017,365 A | 1/2000 | Von Oepen | | 623/1 |
| 6,033,433 A | 3/2000 | Ehr | | 623/1 |
| 6,042,597 A | 3/2000 | Kveen et al. | | 606/198 |
| 6,053,940 A | * 4/2000 | Wijay | | 623/1.15 |
| 6,059,811 A | 5/2000 | Pinchasik et al. | | 606/198 |
| 6,066,169 A | 5/2000 | McGuinness | | 623/1.16 |
| 6,068,656 A | 5/2000 | Von Oepen | | 623/1.17 |
| 6,083,259 A | 7/2000 | Franzen | | 623/1.15 |
| 6,086,604 A | 7/2000 | Fischell et al. | | 606/198 |
| 6,090,127 A | 7/2000 | Globerman | | 606/194 |
| 6,090,133 A | 7/2000 | Richter et al. | | 623/1 |
| 6,099,455 A | 8/2000 | Columbo et al. | | 600/3 |
| 6,106,548 A | 8/2000 | Roubin et al. | | 623/1.15 |
| 6,114,049 A | 9/2000 | Richter | | 428/571 |
| 6,117,156 A | 9/2000 | Richter et al. | | 606/194 |
| 6,117,165 A | 9/2000 | Becker | | 623/1 |
| 6,123,721 A | 9/2000 | Jang | | 623/1 |
| 6,129,754 A | 10/2000 | Kanesaka et al. | | 623/1 |
| 6,156,052 A | 12/2000 | Richter et al. | | 606/191 |
| 6,159,237 A | 12/2000 | Alt et al. | | 623/1.11 |
| 6,171,334 B1 | 1/2001 | Cox | | 623/1.15 |
| 6,179,867 B1 | 1/2001 | Cox | | 623/1.15 |
| 6,179,868 B1 | 1/2001 | Burpee et al. | | 623/1.17 |
| 6,183,506 B1 | * 2/2001 | Penn | | 623/1.15 |
| 6,183,507 B1 | 2/2001 | Lashinski et al. | | 623/1.15 |
| 6,190,403 B1 | 2/2001 | Fischell et al. | | 623/1 |
| 6,190,405 B1 | 2/2001 | Culombo et al. | | 623/1.15 |
| 6,190,406 B1 | 2/2001 | Duerig et al. | | 623/1.2 |
| 6,193,744 B1 | 2/2001 | Ehr et al. | | 623/1 |
| 6,193,747 B1 | 2/2001 | Von Oepen | | 623/1.15 |
| 6,197,048 B1 | 3/2001 | Richter | | 623/1.15 |
| 6,200,334 B1 | 3/2001 | Jang | | 623/1.1 |
| 6,203,569 B1 | 3/2001 | Wijay | | 623/1.15 |
| 6,231,598 B1 | 5/2001 | Berry et al. | | 623/1.15 |
| 6,238,401 B1 | 5/2001 | Richter | | 606/108 |
| 6,251,133 B1 | 6/2001 | Richter et al. | | 623/1.16 |
| 6,273,911 B1 | 8/2001 | Cox et al. | | 623/1.15 |
| 6,287,336 B1 | 9/2001 | Globerman et al. | | 623/1.3 |
| 6,299,755 B1 | 10/2001 | Richter | | 205/651 |
| 6,315,794 B1 | 11/2001 | Richter | | 623/1.34 |
| 6,355,059 B1 | 3/2002 | Richter et al. | | 623/1.17 |
| 6,375,677 B1 | 4/2002 | Penn et al. | | 623/1.16 |
| 6,547,817 B1 | 4/2003 | Fischell et al. | | 623/1.16 |
| 2001/0000043 A1 | 3/2001 | Israel et al. | | 606/198 |
| 2001/0001317 A1 | 5/2001 | Duerig et al. | | 623/1.15 |
| 2002/0052646 A1 | 5/2002 | Fischell et al. | | 623/1.15 |
| 2003/0114868 A1 | 6/2003 | Fischell et al. | | 606/159 |

FOREIGN PATENT DOCUMENTS

| | | | | |
|---|---|---|---|---|
| CA | 2134997 | | 5/1996 | A61F/2/04 |
| CA | 2171047 | | 9/1997 | A61F/2/06 |

| | | | |
|---|---|---|---|
| CA | 2175722 | 11/1997 | A61F/2/04 |
| CA | 2185740 | 3/1998 | A61F/2/06 |
| DE | 295 16712 U1 | 8/1996 | |
| EP | 0 045 627 | 10/1982 | F16L/13/00 |
| EP | 0 505 686 A1 | 9/1992 | A61F/2/06 |
| EP | 0 566 807 A1 | 10/1993 | A61F/2/06 |
| EP | 0 669 114 A1 | 8/1995 | A61F/2/06 |
| EP | 0709067 A2 | 5/1996 | A61F/2/06 |
| FR | 2678508 | 1/1993 | A61F/2/06 |
| JP | 6-41745 | 6/1994 | A61M/29/02 |
| WO | WO 94/12136 | 6/1994 | A61F/21/06 |
| WO | WO 95/09584 | 4/1995 | A61F/2/06 |
| WO | 0669114 | 8/1995 | A61F/2/06 |
| WO | WO95/3194 | 2/1996 | A61F/2/06 |
| WO | WO96/0309 | 2/1996 | A61F/2/02 |
| WO | WO 95/31945 A1 | 2/1996 | A61F/2/06 |
| WO | WO 96/02295 A1 | 2/1996 | A61M/29/02 |
| WO | WO 96/03092 A1 | 2/1996 | A61F/2/02 |
| WO | WO 96/14028 | 5/1996 | A61F/2/06 |
| WO | WO 97/04721 | 2/1997 | A61F/2/06 |
| WO | WO 97/32543 | 9/1997 | A61F/2/06 |
| WO | WO 97/32544 | 9/1997 | A61F/2/06 |
| WO | WO 97/33532 | 9/1997 | A61F/2/06 |
| WO | WO 98/22159 A3 | 5/1998 | A61F/2/06 |
| WO | WO 98/33546 | 8/1998 | A61M/29/00 |
| WO | WO 00/28922 | 5/2000 | |
| WO | WO 00/49971 | 8/2000 | |
| WO | WO 00/53122 | 9/2000 | |
| WO | WO 01/00112 A1 | 1/2001 | |
| WO | WO 01/15632 A1 | 3/2001 | A61F/2/06 |

OTHER PUBLICATIONS

Mirich et al., "Percutaneously Placed Endovascular Grafts for Aortic Aneurysms: Feasibility Study," Radiology, vol. 170, pp. 1033–1037 (1989).

Fallone et al., "Elastic Characteristics of the Self–Expanding Metallic Stents," Investigative Radiology, vol. 23, pp. 370–376 (May 1988).

Charnsangavej et al., "Stenosis of the Vena Cava: Preliminary Assessment of Treatment with Expandable Metallic Stents," Radiology, 1986 161:295–98.

Rösch et al., "Gianturco Expandable Stents in Experimental and Clinical Use," Mar. 24, 1987, pp. 121–124.

Wallace, et al., "Tracheobronchial Tree: Expandable Metallic Stents Used in Experimental and Clinical Applications—Work in Progress," Radiology, 158:309–12 (1986).

Rösch et al., "Experimental Intrahepatic Protacaval Anastomosis: Use of Expandable Gianturco Stents," Radiology, 162:481–85 (1987).

Rösch et al., "Modified Gianturco Expandable Wire Stents in Experimental and Clinical Use," Ann Radiol., 31:100–03 (1988).

Charnsangavej et al., "A New Expandable Metallic Stent for Dilatation of Stenotic Tubular Structures: Experimental and Clinical Evaluation," Houston Medical Journal, vol. 3, Jun. 1987, pp. 41–51.

Rösch et al., "Gianturco Expandable Wire Stents in the Treatment of Superior Vena Cava Syndrome Recurring After Maximum–Tolerance Radiation," Cancer, 60:1243–46 (1987).

Yoshioka et al., "Self–Expanding Endovascular Graft: An Experimental Study in Dogs," AJR, 151:673–76 (1988).

Simonds et al., "Use of Expandable Metal Stents in the Treatment of Bronchial Obstruction," THORAX, 44:680–81 (1989).

Duprat et al., "Flexible Balloon–Expanded Stent for Small Vessels—Work in Progress," Radiology, 162:276–78 (1987).

* cited by examiner

A ▨  B ▨

EXPANDABLE STENT AND METHOD FOR DELIVERY OF SAME

This application is a continuation of application Ser. No. 09/142,509, filed Feb. 18, 1999 (now U.S. Pat. No. 6,183, 506, issued Feb. 6, 2001), which is a 371 of PCT/CA97/00152), filed Mar. 5, 1997 (designating the U.S.; and published in English as WO 97/32544 on Sep. 12, 1997), which claims benefit of (i) CA 2,171,047, filed Mar. 5, 1996, (ii) CA 2,175,722, filed May 3, 1996, (iii) CA 2,185,740, filed Sep. 17, 1996, and (iv) CA 2,192,520, filed Dec. 10, 1996.

TECHNICAL FIELD

The present invention relates to an expandable stent.

BACKGROUND ART

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g. a lumen or artery).

In the past six to eight years, the use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g. natural or iatrogenic) within the human body and can include a member selected from the group comprising: blood vessels, respiratory ducts, gastrointestinal ducts and the like.

Initial stents were self-expanding, spring-like devices which were inserted in the body passageway in a contracted state. When released, the stent would automatically expand and increase to a final diameter dependent on the size of the stent and the elasticity of the body passageway. An example of such a stent is known in the art as the Wallstent™.

The self-expanding stents were found by some investigators to be deficient since, when deployed, they could place undue, permanent stress on the walls of the body passageway. Further, upon expansion, the stent would shorten in length in an unpredictable fashion thereby reducing the reliability of the stent. This led to the development of various stents which were controllably expandable at the target body passageway so that only sufficient force to maintain the patency of the body passageway was applied in expanding the stent.

Generally, in these later systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby expanding the stent by plastic deformation so that the latter is urged in place against the body passageway. As indicated above, the amount of force applied is at least that necessary to maintain the patency of the body passageway. At this point, the balloon is deflated and withdrawn within the catheter, and subsequently removed. Ideally, the stent will remain in place and maintain the target area of the body passageway substantially free of blockage (or narrowing).

A stent which has gained some notoriety in the art is known as the Palmaz-Schatz™ Balloon Expandable Stent (hereinafter referred to as "the Palmaz-Schatz stent"). This stent is discussed in a number of patents including U.S. Pat. Nos. 4,733,665, 4,739,762, 5,102,417 and 5,316,023, the contents of each of which are hereby incorporated by reference.

Another stent which has gained some notoriety in the art is known as the Gianturco-Roubin Flex-Stent™ (hereinafter referred to as "the Gianturco-Roubin stent"). This stent is discussed in a number of patents, including U.S. Pat. Nos. 4,800,882, 4,907,336 and 5,041,126, the contents of each of which are hereby incorporated by reference.

Other types of stents are disclosed in the following patents:

U.S. Pat. No. 5,035,706 (Gianturco et al.),
U.S. Pat. No. 5,037,392 (Hillstead),
U.S. Pat. No. 5,147,385 (Beck et al.),
U.S. Pat. No. 5,282,824 (Gianturco),
Canadian patent 1,239,755 (Wallsten), and
Canadian patent 1,245,527 (Gianturco et al.), the contents of each of which are hereby incorporated by reference.

While these prior art stents have achieved a varying degree of success, the art is constantly in need of new stents having improved flexibility and stability while being able to be readily implanted with little or no trauma to the target lumen.

In our Canadian patent application number 2,134,997 (Penn et al.), the contents of which are hereby incorporated by reference, there is described an improved expandable stent. The stent comprises a tubular wall disposed between the proximal end and the distal end. The tubular wall has a longitudinal axis and a porous surface defined by a plurality intersecting members arranged to define a first repeating pattern. The first repeating pattern comprises a polygon having a pair of side walls substantially parallel to the longitudinal axis. A first concave-shaped wall and a second convex-shaped wall connect the side walls. The first wall and the second wall are equidistant along an axis which is parallel to the longitudinal axis. The stent is expandable from a first, contracted position to a second, expanded position upon the application of a radially outward force exerted on the stent.

As disclosed in the '997 application, the first repeating pattern can be implemented in, inter alia, a mono-tubular expandable stent and a bifurcated expandable stent.

While the stent disclosed in the '997 application is an advance in the art, in certain cases, a significant force is required to achieve expansion in the target body passageway. Further, implantation of the stent disclosed in the '997 application can be difficult in certain situations where the unexpanded stent must travel through a significantly curved pathway to the target body passageway.

Accordingly, it would be desirable to have an improved stent which overcomes these disadvantages. It would be further desirable if the improved stent could be readily adapted, inter alia, to mono-tubular expandable stents and bifurcated expandable stents. The latter type of stents would be useful in treating aneurysms, blockages and other ailments. It would also be desirable if such a stent was relatively easy to implant. It would be further desirable if such a stent were capable of being uniformly expanded at relatively low pressure while obviating or mitigating longitudinal shrinkage thereof. It would be further desirable if such a stent were not susceptible to asymmetric internal coverage of the body passageway, a problem associated with "coil"-type stents—see, for example, U.S. Pat. No. 5,282, 824 (Gianturco). It would be further desirable if such a stent was not susceptible to movement along the longitudinal axis of the body passageway during or after implantation. It would be further desirable if such a stent was characterized by a desirable balance of lateral flexibility in the unexpanded state and radial rigidity in the expanded state.

DISCLOSURE OF THE INVENTION

It is an object of the present invention to provide a novel expandable stent which obviates or mitigates at least one of the above-mentioned disadvantages of the prior art.

Accordingly, in one of its aspects, the present invention provides an expandable stent comprising a proximal end and a distal end in communication with one another, a tubular wall disposed between the proximal end and the distal end, the tubular wall having a longitudinal axis and a porous surface defined by a plurality of intersecting members comprising a series of longitudinal struts disposed substantially parallel to the longitudinal axis of the stent, each of the longitudinal struts comprising flexure means for substantially complementary extension and compression of a diametrically opposed pair of the longitudinal struts upon flexure of the stent, the stent being expandable from a first, contracted position to a second, expanded position upon the application of a radially outward force on the stent.

Thus, in this aspect of the present invention, we have now discovered that the use of flexure means in the series of longitudinal struts leads to a very desirable balance of lateral flexibility of the unexpanded stent and radial rigidity of the expanded stent. Practically, the flexure means confers lateral flexibility to the unexpanded stent by allowing diametrically opposed pairs of the longitudinal struts to undergo substantially complementary extension and compression. If one considers a stent in a flexed state, a first longitudinal strut disposed at the tangent of the bend (i.e. in two dimensions) will expand in response to the bending moment. In contrast, a second longitudinal strut disposed diametrically opposite (this can mean above, below or in the same radial plane as) the first longitudinal strut will compress in response to the bending bend moment. Generally, the degree of extension and compression will be substantially complementary. In other words, in most cases, the first longitudinal strut will expand and lengthen a first distance and the second longitudinal strut will compress and shorten a second distance. Preferably, the first distance is greater than the second distance and most preferably, the sum of the first distance and the second distance is substantially equal to the sum of the original lengths of the first longitudinal strut and the second longitudinal strut.

The specific shape of the flexure means disposed in the longitudinal strut is not particularly restricted provided that it confers lateral flexibility to the unexpanded stent by allowing diametrically opposed pairs of the longitudinal struts to undergo substantially complementary extension and compression. The term "diametrically opposed pairs of the longitudinal struts", as used in this specification, is intended to have a broad meaning. Thus, the "pair" can include opposed struts in the same horizontal plane (i.e. the same ring of polygons) or in different horizontal planes (e.g. one strut in a first ring of polygons and the other diametrically opposed strut in a second ring of polygons above or below the first ring). Preferably, the flexure means comprises at least one lateral section disposed in the longitudinal strut, more preferably at least a first lateral section and a second lateral section disposed in the longitudinal strut. By "lateral section" is meant a section of the longitudinal strut which is bowed in or out of (i.e. radially from) the strut. The apex of the lateral section may be pointed, rounded or substantially flat. When the flexure means comprises a first lateral section and a second lateral section, the two sections may be symmetric or asymmetric (in the case of asymmetric this includes two sections of the same shape but different size and two sections of different and size). Further, when the flexure means comprises a first lateral section and a section lateral section, the sections may be bowed in the same or opposite direction.

A particularly preferred embodiment of the flexure means comprises a sinusoidal or S-shaped section (various examples of such a section are illustrated herein and discussed below). Preferably, the sinusoidal or S-shaped section is adjacent the second apex of the polygon and the remaining portion of the strut is substantially straight. This feature improves the lateral flexibility of the stent thereby facilitating implantation thereof and may further mitigate longitudinal shortening of the stent upon expansion.

In another preferred embodiment, at least one, more preferably both, of the side walls (i.e. longitudinal struts) of the polygon comprises the sinusoidal or S-shaped section. Preferably, the sinusoidal or S-shaped section is disposed at an end of the side wall. This feature improves the lateral flexibility of the stent thereby facilitating implantation thereof and may further mitigate longitudinal shortening of the stent upon expansion.

When a sinusoidal or S-shaped portion is disposed in the side walls and/or the strut connecting the first apex and the second apex (if present), the precise shape of the portion is not particularly restricted and generally takes the form of an "S". Thus, the sinusoidal or S-shaped portion may be comprised of a pair of joined curved sections wherein each curved section has an arc of about 180°—i.e. this is illustrated in FIG. 8 of the present application. The term "arc" denotes the angle from one end of the curved section to the other about the radical point of the curved section. Alternatively, the sinusoidal or S-shaped portion may be comprised of a pair of joined curved sections wherein each curved section has an arc of greater than 180°—this is illustrated in FIG. 9 of the present application. Further the pair of joined curved sections can be of the same size (this is illustrated in FIGS. 8 and 9 of the present application) or of differing size (this is illustrated in FIG. 10 of the present application), the latter being the most preferred embodiment.

Preferably, the series of longitudinal struts containing the flexure means comprises all substantially longitudinal struts comprised in the plurality of intersecting members making up the porous surface of the stent.

Preferably, for this aspect of the present invention, the intersecting members are arranged to define a first repeating pattern comprised of a polygon having a pair of side walls substantially parallel to the longitudinal axis (i.e. a pair of the above-mentioned longitudinal struts comprising flexure means), a concave-shaped first wall having a first apex and a convex-shaped second wall having a second apex connecting the side walls. As used throughout this specification, the terms "concave-shaped" and "convex-shaped" are intended to have a broad meaning and a shape having apex. Thus, the first wall has a first apex and the second wall has a second apex. Thus, the first apex (i.e. of the concave-shaped first wall) is directed into the polygon whereas the second apex (i.e. of the convex-shaped second wall) is directed away from the polygon.

In another of its aspects, the present invention provides an expandable stent comprising a proximal end and a distal end in communication with one another, a tubular wall disposed between the proximal end and the distal end, the tubular wall having a longitudinal axis and a porous surface defined by a plurality of intersecting members arranged to define a first repeating pattern comprised of a polygon having a pair of side walls substantially parallel to the longitudinal axis, a concave-shaped first wall having a first apex and a convex-shaped second wall having a second apex, the first wall and the second wall connecting the side walls, at least one of the first apex and the second apex being substantially flat, the stent being expandable from a first, contracted position to a second, expanded position upon the application of a radially outward force on the stent.

In this aspect of the invention, it is has been discovered that the use of such a first repeating pattern (including at least one of the first apex and second apex being substantially flat), with or without the flexure means present in the side walls of the polygon in the first repeating pattern, results in an improved stent. The advantages associated with the use of such a such a first repeating pattern include the following:

1. the force required to expand the stent is substantially reduced;
2. the stent is subjected to less traumatic stress during expansion;
3. plastic deformation of the stent during expansion is facilitated;
4. construction of the stent is facilitated; and
5. upon expansion of the stent, warpage of the first apex and the second apex is obviated or mitigated.

The provision of at least one of the first apex and the second apex being substantially flat usually results in the apex of the concave-shaped first wall and/or the convex-shaped second wall having a pair of shoulders. Preferably, these shoulders are rounded. The provision of such round shoulders results in the following additional advantages:

6. mitigation of potential trauma to the target body passageway from: (i) endoluminal contents within the passageway, and (ii) the contours of the passageway;
7. the resulting expanded stent is more stream-lined and flow-directed which mitigates potential trauma to the target body passageway;
8. further reduction in the force required to expand the stent;
9. an improved stent expansion ratio is achieved (i.e. ratio of expanded stent diameter at maximum expansion to unexpanded stent diameter);
10. upon expansion of the stent, the concave-shaped first wall and the convex-shaped second wall are in a substantially orthogonal relationship to the longitudinal axis thereby improving the rigidity of the stent (this is very important to mitigate the occurrence of stent recoil); and
11. the pattern of the expanded stent improves the rheology of fluid flow in the body passageway.

When the stent of the present invention includes the above-mentioned first repeating pattern, it is preferred to provide a connecting strut between the first apex and the second apex. Generally, the connecting strut will be substantially longitudinal (i.e. it will be parallel to the longitudinal axis of the stent). This feature mitigates lifting of the shoulders referred to above as the stent is flexed, for example, when passing the stent through a curved body passageway. The result of this is that potential trauma to the body passageway is mitigated since scraping of the body passageway by the shoulders is mitigated.

In a preferred embodiment, the connecting strut is curved with respect to the longitudinal axis (this is described and illustrated hereinbelow). Preferably, the strut is sufficiently curved to have a length of up to about 35%, more preferably up to about 15%, even more preferably in the range of from about 2% to about 8%, most preferably in the range of from about 3% to about 7%, greater than the distance between the first apex and the second apex. This feature improves the lateral flexibility of the stent thereby facilitating implantation thereof. In some cases, the curvature may be designed to comprise the flexure means discussed above. In other words, the shape of the curvature may be designed substantially complementary extension and compression of the connecting strut upon flexure of the stent.

Yet another preferred feature of the stent of the present invention is the provision of one or both of the side walls of the polygon of the repeating pattern being curved. Preferably, both side walls are curved. More preferably the curvature serves as flexure means as described above. Ideally, the curved side wall has length of up to about 35%, more preferably up to about 15%, even more preferably in the range of from about 2% to about 8%, most preferably in the range of from about 3% to about 7%, greater than the distance between the termini of the concave-shaped first wall and the concave-shaped second wall. This feature improves the lateral flexibility of the strut thereby facilitating implantation thereof.

Preferably, both the strut and the side walls are curved. More preferably, each of the curved members are of substantially the same length.

Yet another preferred feature of the stent of the present invention is, in addition to the strut and side walls of the polygon being curved, the provision of all longitudinal walls of the polygon of the repeating pattern being curved. Thus, in this embodiment of the invention, the concave-shaped first wall comprises a pair of curved first apex walls connecting the first apex and the side walls of the polygon, and the convex-shaped second wall comprises a pair of curved second apex walls connecting the second apex and the side walls of the polygon. Again, in some cases, the curvature may be designed to comprise the flexure means discussed above. Ideally, the curved first apex walls and the curved second apex walls each have a length of up to about 35%, more preferably up to about 15%, even more preferably in the range of from about 2% to about 8%, most preferably in the range of from about 3% to about 7%, greater than the straight (i.e. non-curved) distance between the first apex and the side walls, and the second apex and the side walls, respectively. In this embodiment, it is further preferred to have substantially all adjacent curved walls in an annular section of the repeating pattern (i.e. of the struts, first apex wall, second apex wall and side walls) are substantially equidistant from one another. This preferred feature of the stent of the present invention even further enhances the lateral flexibility of the stent thereby further facilitating implantation thereof.

Yet another preferred feature of the stent of the present invention is provision of a porous surface comprising multiple designs. Specifically, in certain cases, it may be desirable to design the stent to varying degrees of relative flexibility and rigidity along the length thereof. Thus, the relatively flexible portion(s) of such a stent would facilitate delivery of the stent to a target body passageway through a relatively tortuous route, while the relatively rigid portion(s) of the stent serves facilitate maintaining the patency of the body passageway. As will be discussed in more detail hereinbelow, this may be achieved by varying the repeating pattern design along the longitudinal length of the stent.

An aspect of the present invention relates to the provision of an expandable bifurcated stent. As used throughout this specification, the term "bifurcated stent" is intended to have a broad meaning and encompasses any stent having a primary passageway to which is connected at least two secondary passageways. Thus, trifurcated stents are encompassed herein. Further, one of the secondary passageways can be a continuation of the primary passageway with the result that the other secondary passageway is essentially a side branch to the primary passageway.

The stent of the present invention (bifurcated or monotubular) can further comprise coating material thereon. The coating material can be disposed continuously or discontinuously on the surface of the stent. Further, the coating may be disposed on the interior and/or the exterior surface(s) of the stent. The coating material can be one or more of a biologically inert material (e.g. to reduce the thrombogenicity of the stent), a medicinal composition which leaches into the wall of the body passageway after implantation (e.g. to provide anticoagulant action, to deliver a pharmaceutical to the body passageway and the like) and the like.

The stent is preferably provided with a biocompatible containing, in order of minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably however the polymer has zwitterionic pendant groups, generally ammonium phosphate ester groups, for instance phosphoryl choline groups or analogues thereof. Examples of suitable polymers are described in International application number WO-A-93/16479 and WO-A-93/15775. Polymers described in those specifications are hemo-compatible as well as generally biocompatible and, in addition, are lubricious. It is important to ensure that the surfaces of the stent are completely coated in order to minimize unfavourable interactions, for instance with blood, which might lead to thrombosis.

This good coating can be achieved by suitable selection of coating conditions, such as coating solution viscosity, coating technique and/or solvent removal step.

In another embodiment of the invention, the stent may be joined to a polymer material. Specifically, a polymer material may be extruded onto the stent in such a manner that it envelops at least a portion of the stent. This technique may be used to join two or more stents with a flexible polymeric tube. This technique may also be used to join a stent to another prosthetic device such as a tube, a graft and the like. Thus, in this embodiment of the invention, the stent is incorporated into an endoluminal prosthesis.

In yet another embodiment of the invention the stent may be secured (e.g. by suturing) to an existing endoluminal prosthesis such as Gortex™ material or to biological material such as basilic vein. In this regard, securing of the stent to the existing endoluminal prosthesis or biological material may be facilitated by designing the stent such that an end of the stent comprises an annular row of the above-mentioned polygons is having a convex-shaped wall with a flat apex.

BRIEF DESCRIPTION OF THE DRAWINGS

Embodiments of the present invention will be described with reference to the accompanying drawings wherein like numerals designate like parts and in which.

BEST MODE FOR CARRYING OUT THE INVENTION

Figure 1:
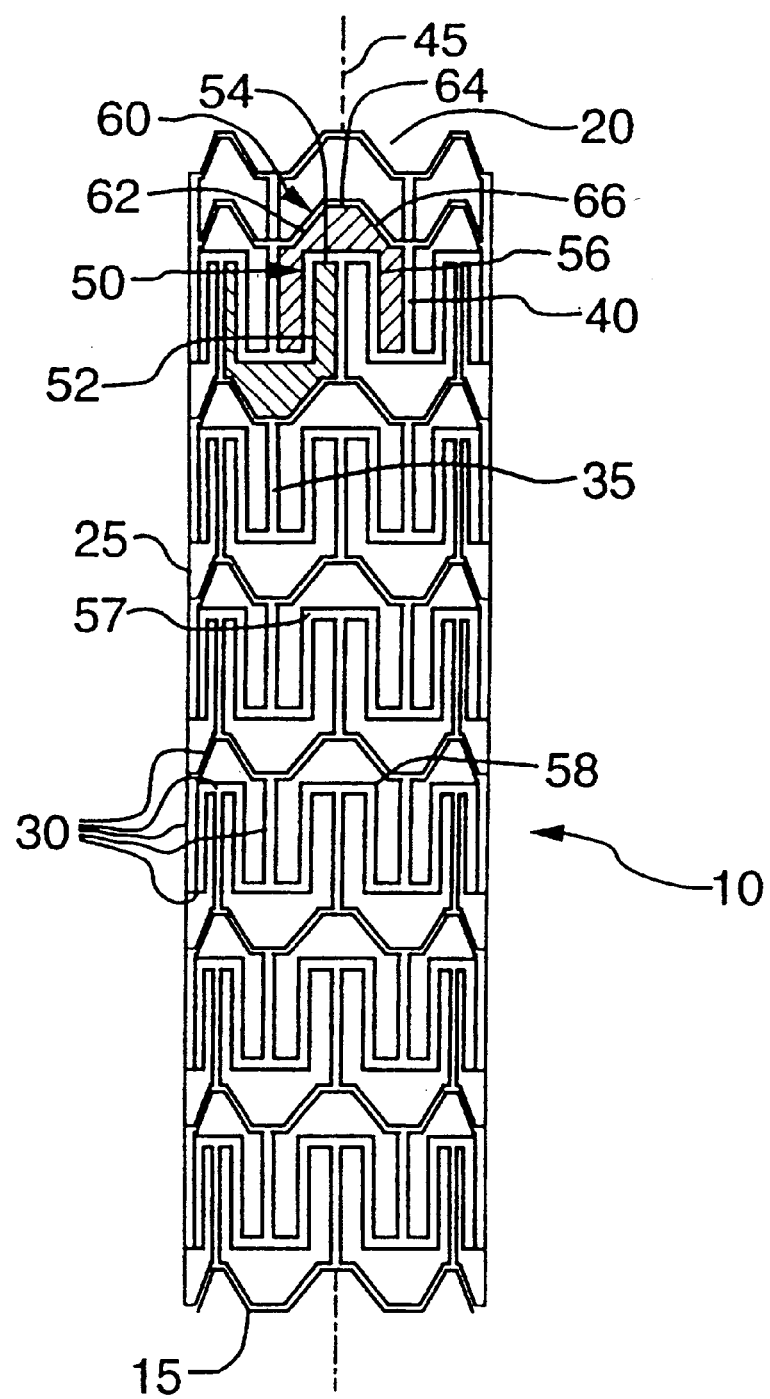
FIG. 1 illustrates an exploded perspective view of a mono-tubular stent prior to expansion.
Figure 1:

With reference to FIG. 1, there is illustrated a stent 10. Stent 10 comprises a proximal end 15 and a distal end 20. Stent further comprises a tubular wall 25 disposed between proximal end 15 and distal end 20. As illustrated, tubular wall 25 is porous. The porosity of tubular wall 25 is defined by a plurality of intersecting members 30. Intersecting members 30 define a first repeating pattern designated A in FIG. 1.

Figure 1A:
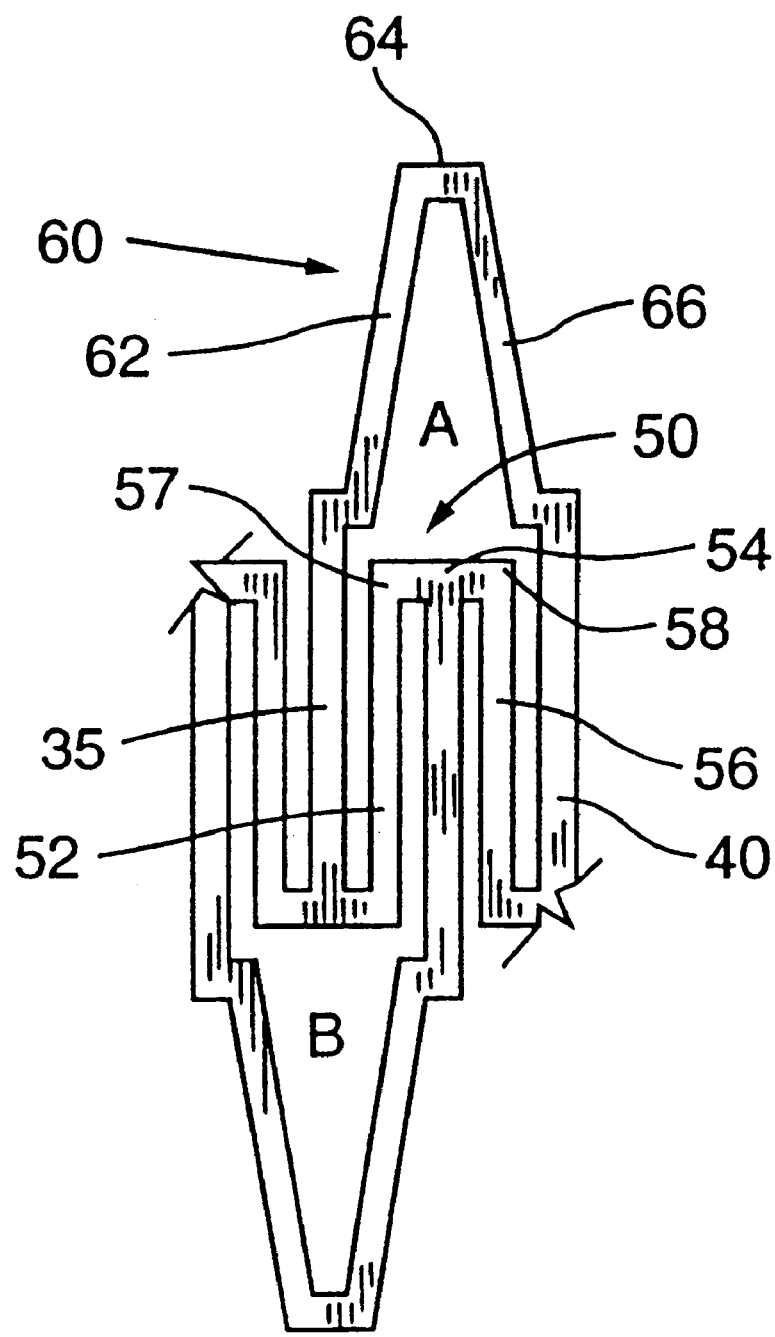
FIG. 1A illustrates an exploded view of a portion of the stent illustrated in FIG. 1.

As illustrated and with further reference to FIG. 1A, repeating pattern A is a polygon comprising a pair of side walls 35,40. Side walls 35,40 are substantially parallel to a longitudinal axis 45 of stent 10 and thus side walls 35,40 may be considered to be longitudinal struts (indeed with reference to each of the drawings, side walls may also be considered to be longitudinal struts). Side walls 35,40 are connected by a concave-shaped wall 50 and a convex-shaped wall 60.

As illustrated, concave-shaped wall 50 is made up of a trio of segments 52,54,56. In the illustrated embodiment, segment 54 is the apex of concave-shaped wall 54. As is evident, segment 54 is a flat apex and results in the provision of a pair of substantially square shoulders 57,58. Convex-shaped wall 60 is made up of a trio of segments 62,64,66. In the illustrated embodiment, segment 64 is the apex of convex-shaped wall 60.

It will be appreciated by those of skill in the art that the provision of first repeating pattern A, as illustrated, necessarily defines and provides for a second repeating pattern B. It will also be appreciated by those of skill in the art that second repeating pattern B is a mirror image of first repeating pattern A taken along an axis (not shown) substantially normal to longitudinal axis 45. Thus, in the illustrated embodiments, adjacent rows of repeating pattern A and repeating pattern B may be considered to by interlocking polygons or "arrowheads".

It will be further appreciated by those of skill in the art that the shape of concave-shaped wall 50 and/or convex-shaped wall 60 can be modified without departing from the function and performance of the stent provided that at least one of concave-shaped wall 50 and convex-shaped wall 60 retain a substantially flat apex. For example, the trio of segments can be replaced by a suitably curved or arcuate wall. Alternatively, more than three segments can be used to define concave-shaped wall 50 and/or convex-shaped wall 60. Other modifications will be apparent to those of skill in the art.

It will be further appreciated by those of skill in the art that various walls of first repeating pattern A and second repeating pattern B may be omitted (and even desired) at selected points along the body of the stent without departing from the spirit and scope of the invention. For example, it is possible to omit one or both of side walls 35 and 40 at selected points along the body of the stent with a view to improving the longitudinal flexibility of the stent. Further, it is possible to omit one or more of segments 62,64,66 at selected points along the body of the stent with a view to improving the lateral flexibility of the stent.

Still further, the stent depicted in FIG. 1 can be modified to omit, on a selected basis, first repeating pattern A and/or second repeating B with a view to improve flexibility of the stent and to allow access to other structures (e.g. side branches/arteries) outside the bounds of the stent.

With reference to FIGS. 2–10, there are illustrated a number of preferred embodiments of repeating pattern A. For the sake of clarity, numerals in FIGS. 2–8 have the same final two digits as the corresponding numerals in FIG. 1. Thus, for example, the concave-shaped wall is depicted as element 50 in FIG. 1, element 150 in FIG. 2, element 250 in FIG. 3, etc.

Figure 2:
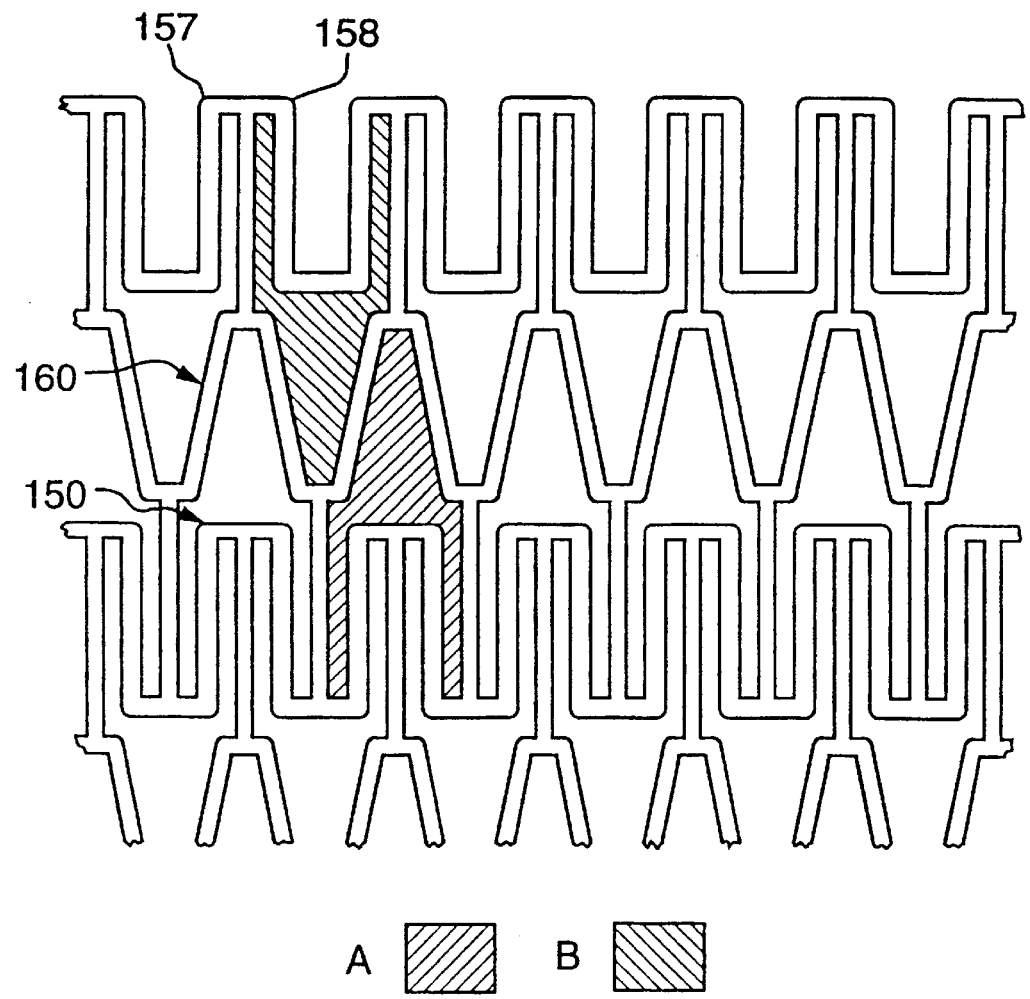
FIGS. 2–10 each illustrate a two dimensional representation of various embodiments (not to relative scale) of a repeating pattern useful in the stent of the present invention.

Thus, as illustrated in FIG. 2, repeating pattern A is comprised of a concave-shaped wall 150 and a convex-shaped wall 160, the former having a flat apex. Further, as illustrated, concave-shaped wall 150 and convex-shaped wall 160 are not equidistant along an axis orthogonal to the longitudinal axis of the stent (not shown). Thus, in this embodiment, the flat apex in concave-shaped wall 150 has been modified such that it comprises a pair of substantially rounded shoulders 157,158.

Figure 3:
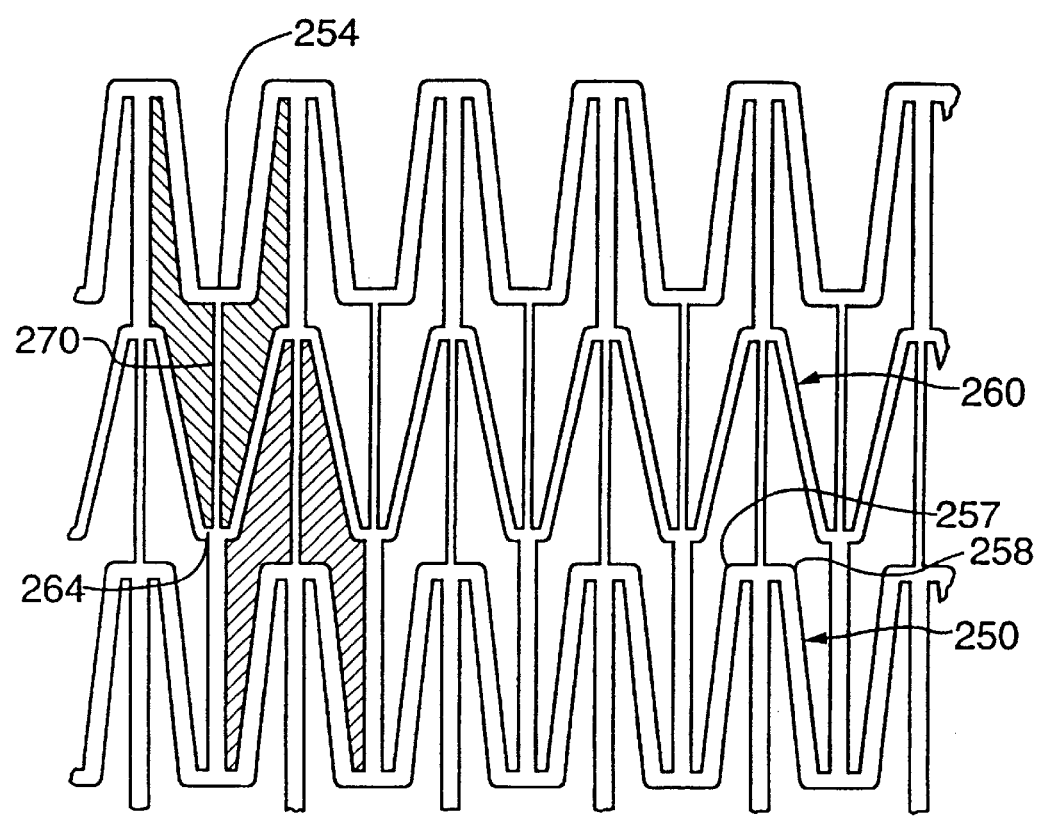

With reference to FIG. 3, repeating pattern A is similar to the one illustrated in FIG. 1. In FIG. 3, the flat apex of concave-shaped wall 250 has been modified to provide a pair of rounded shoulders 257,258. Further, a strut 270 has been added to connect segment 254 of concave-shaped wall 250 and segment 264 of convex-shaped wall 260. As illustrated, strut 270 is thinner in dimension that any of the segments making up concave-shaped wall 250 and convex-shaped wall 260. Thus, strut 270 may be considered as a relatively thin retention wire which reconciles the need for retaining flexibility in the strut with mitigating lifting of rounded shoulders 257,258 when the stent is delivered to the target body passageway through a relatively tortuous route.

Figure 4:
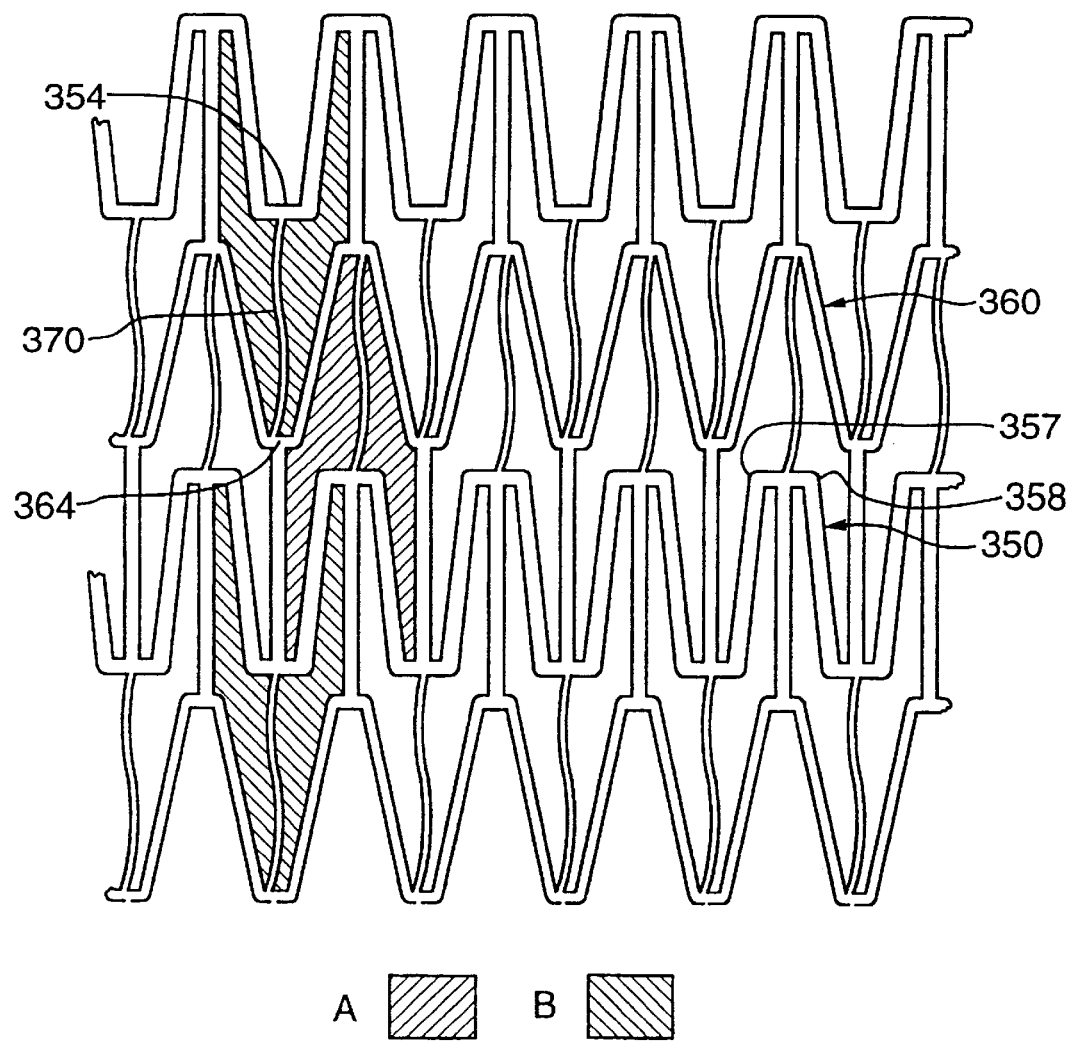

With reference to FIG. 4, repeating pattern A is similar to the one illustrated in FIG. 1. In FIG. 4, the flat apex of concave-shaped wall 350 has been modified to provide a pair of rounded shoulders 357,358. Further, a curved strut 370 has been added to connect segment 354 of concave-shaped wall 350 and segment 364 of convex-shaped wall 360.

Figure 5:
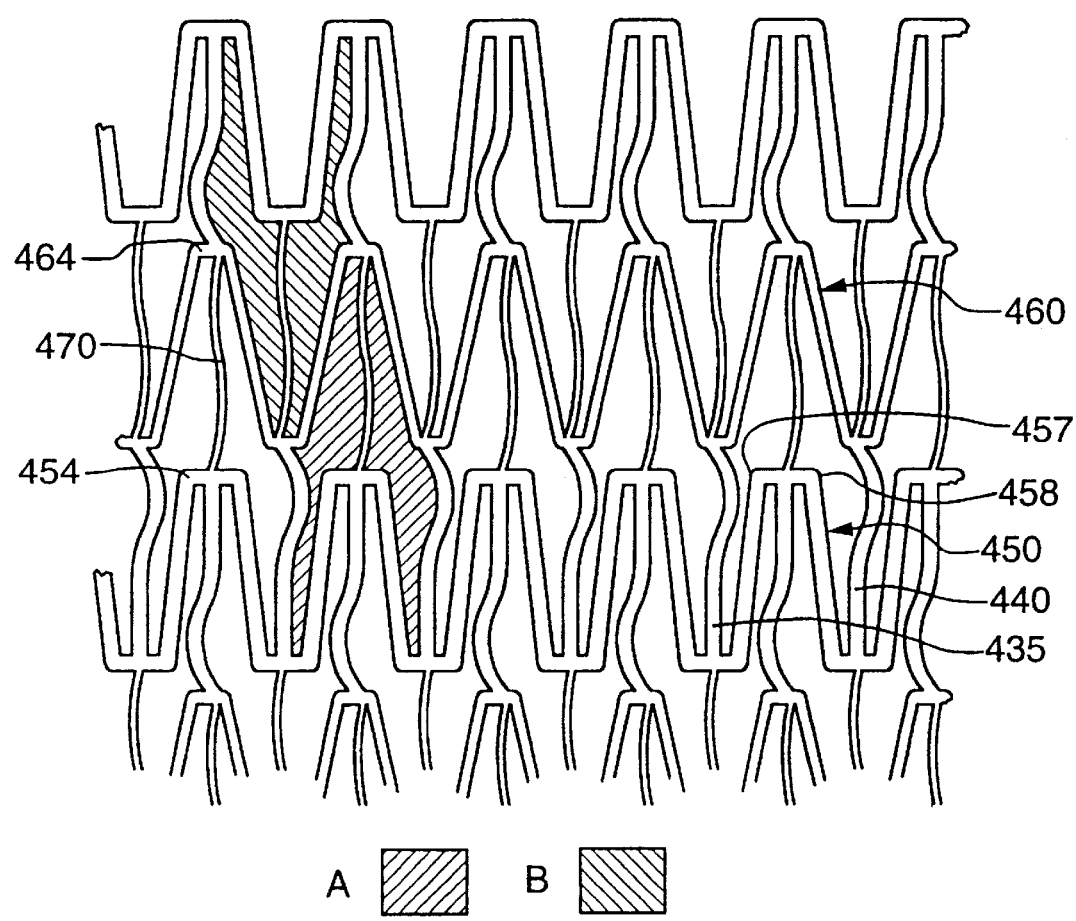

With reference to FIG. 5, repeating pattern A is similar to the one illustrated in FIG. 1. In FIG. 5, the flat apex of concave-shaped wall 450 has been modified to provide a pair of rounded shoulders 457,458. Further, a curved strut 470 has been added to connect segment 454 of concave-shaped wall 450 and segment 464 of convex-shaped wall 460. Further, side walls 435,440 are also curved. As discussed above, since side walls 435,440 are bowed in opposite directions in adjacent rows of repeating pattern A and B, substantially diametric side walls in adjacent rows will function as the flexure means described above.

Figure 6:
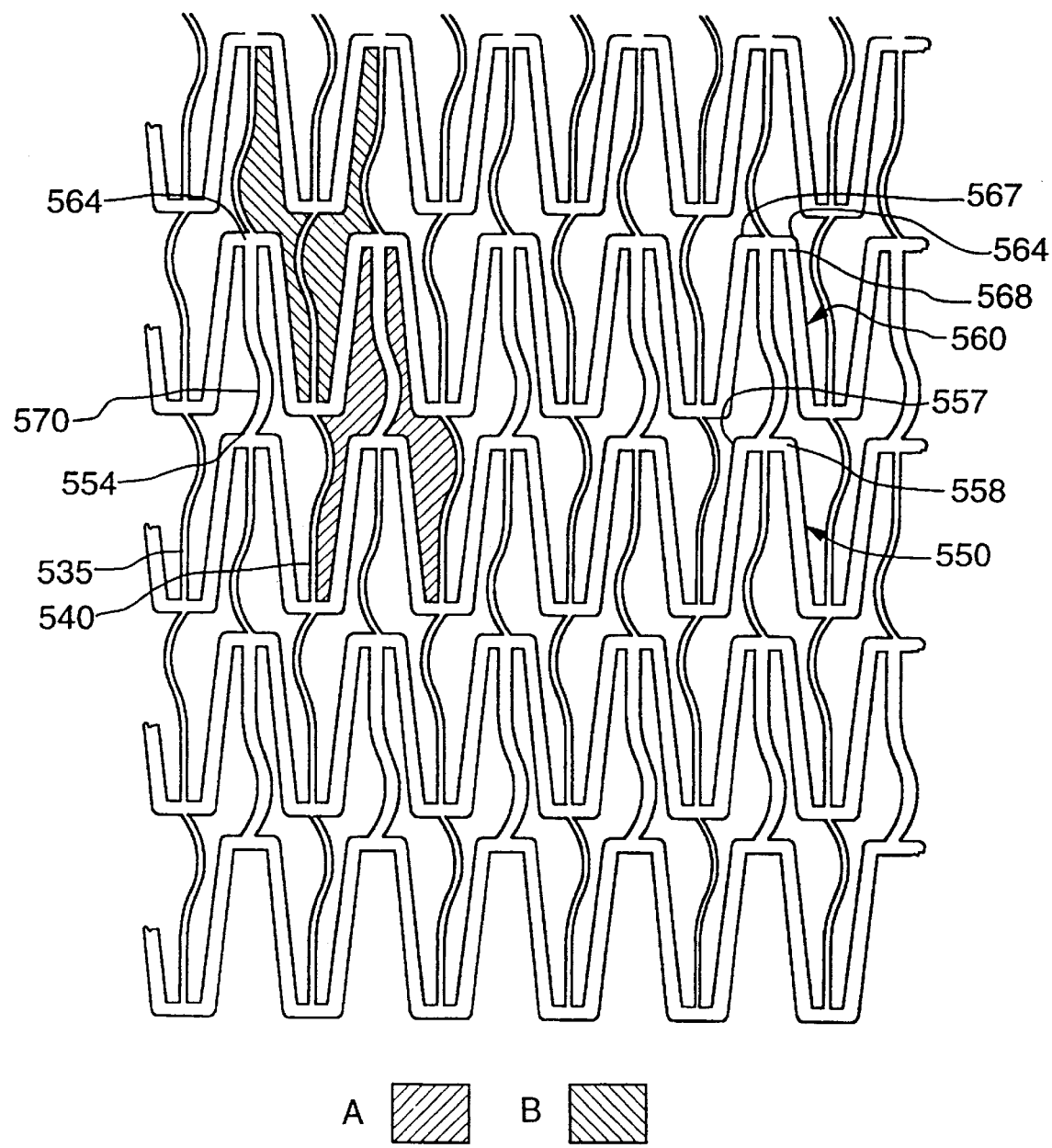

With reference to FIG. 6, repeating pattern A is similar to the one illustrated in FIG. 1. In FIG. 6, concave-shaped wall 550 has been modified to have a flat apex 554 having a pair of rounded shoulders 557,558 and convex-shaped wall 560 has been modified also to have a flat apex 564 having a pair of rounded shoulders 567,568. Further, a curved strut 570 has been added to connect flat apex 554 of concave-shaped wall 550 and flat apex 564 of convex-shaped wall 560. Further, side walls 535,540 are also curved.

Figure 7:
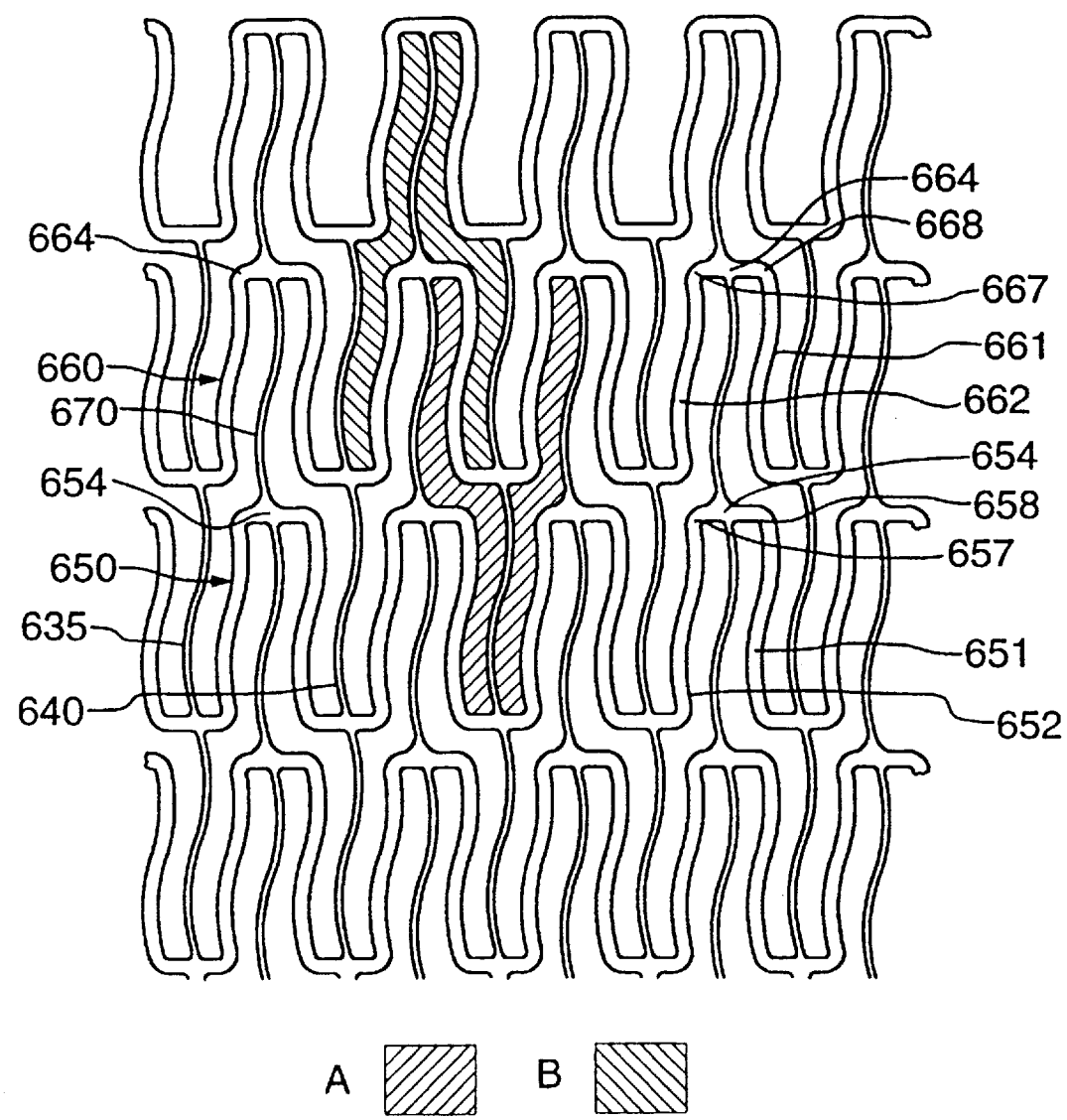

With reference to FIG. 7, repeating pattern A is similar to the one illustrated in FIG. 1. In FIG. 7, concave-shaped wall 650 has been modified to have a flat apex 654 having a pair of rounded shoulders 657,658 and convex-shaped wall 660 has been modified also to have a flat apex 664 having a pair of rounded shoulders 667,668. Further, a curved strut 670 has been added to connect flat apex 654 of concave-shaped wall 650 and flat apex 664 of convex-shaped wall 660. Further, side walls 635,640 are also curved. Still further, walls 661,662 which connect flat apex 664 to side walls 635,640, respectively, and walls 651,652 which connect flat apex 654 to side walls 635,640, respectively, are each curved. It is believed that this design even further enhances the lateral flexibility of the stent.

Figure 8:
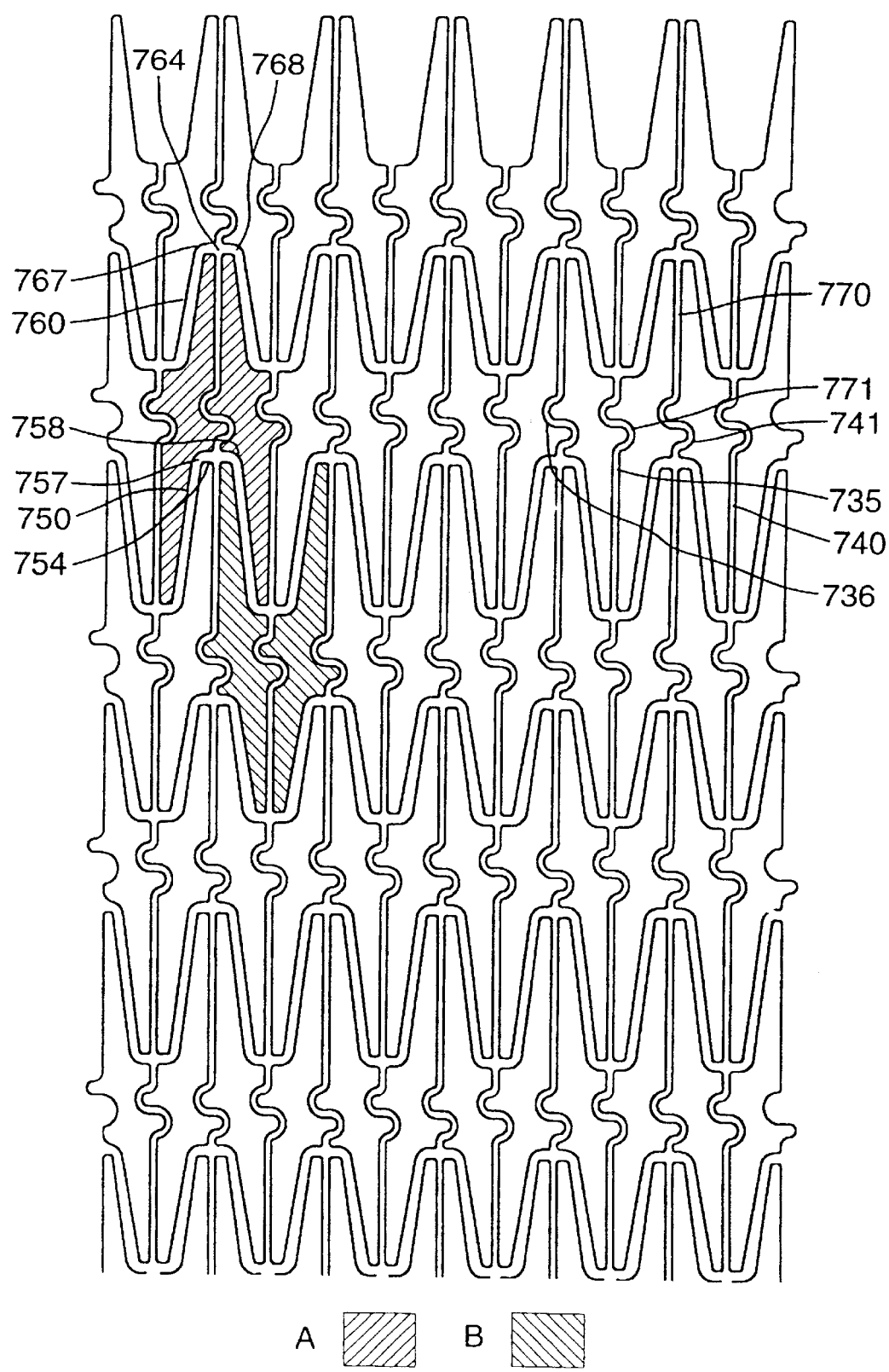

With reference to FIG. 8, repeating pattern A is similar to the one illustrated in FIG. 1. In FIG. 7, concave-shaped wall 750 has been modified to have a flat apex 754 having a pair of rounded shoulders 757,758 and convex-shaped wall 760 has been modified also to have a flat apex 764 having a pair of rounded shoulders 767,768. Further, a strut 770 has been added to connect flat apex 754 of concave-shaped wall 750 and flax apex 764 of convex-shaped wall 760. Further, side walls 735,740 have been modified to include a sinusoidal (or S-shaped) portion 736,741, respectively, adjacent convex-shaped wall 760. Further, strut 770 has been modified to include a sinusoidal (or S-shaped) portion 771 adjacent flat apex of concave-shaped wall 750. This design even further enhances the lateral flexibility of the stent.

Figure 9:
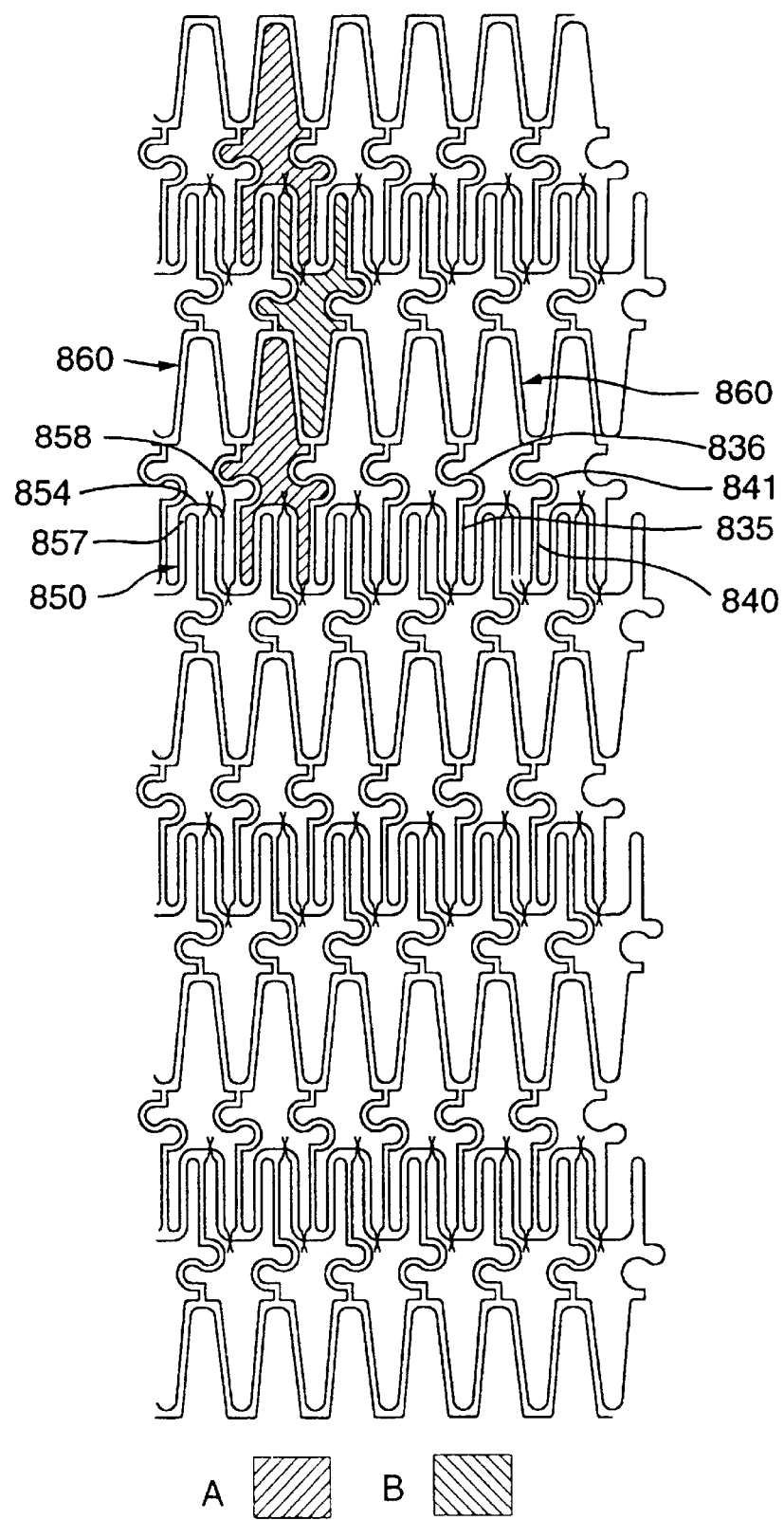

With reference to FIG. 9, repeating pattern A is similar to the one illustrated in FIG. 1. In FIG. 9, concave-shaped wall 850 has been modified to have a flat apex 854 having a pair of rounded shoulders 857,858. Further, side walls 835,840 have been modified to include a pair of sinusoidal (or S-shaped) portions 836,841, respectively, adjacent convex-shaped wall 860. This design further enhances the lateral flexibility of the stent illustrated in FIG. 2. It should be noted that each sinusoidal (or S-shaped) portion 836,841 in FIG. 9 comprises a pair of adjoined curved sections wherein each curved section has an arc of greater than 180°—another way to conceptualize this is a pair of link omega-shaped sections (cf. with the curved sections of sinusoidal (or S-shaped) portions 736,741,771 in FIG. 8).

Figure 10:
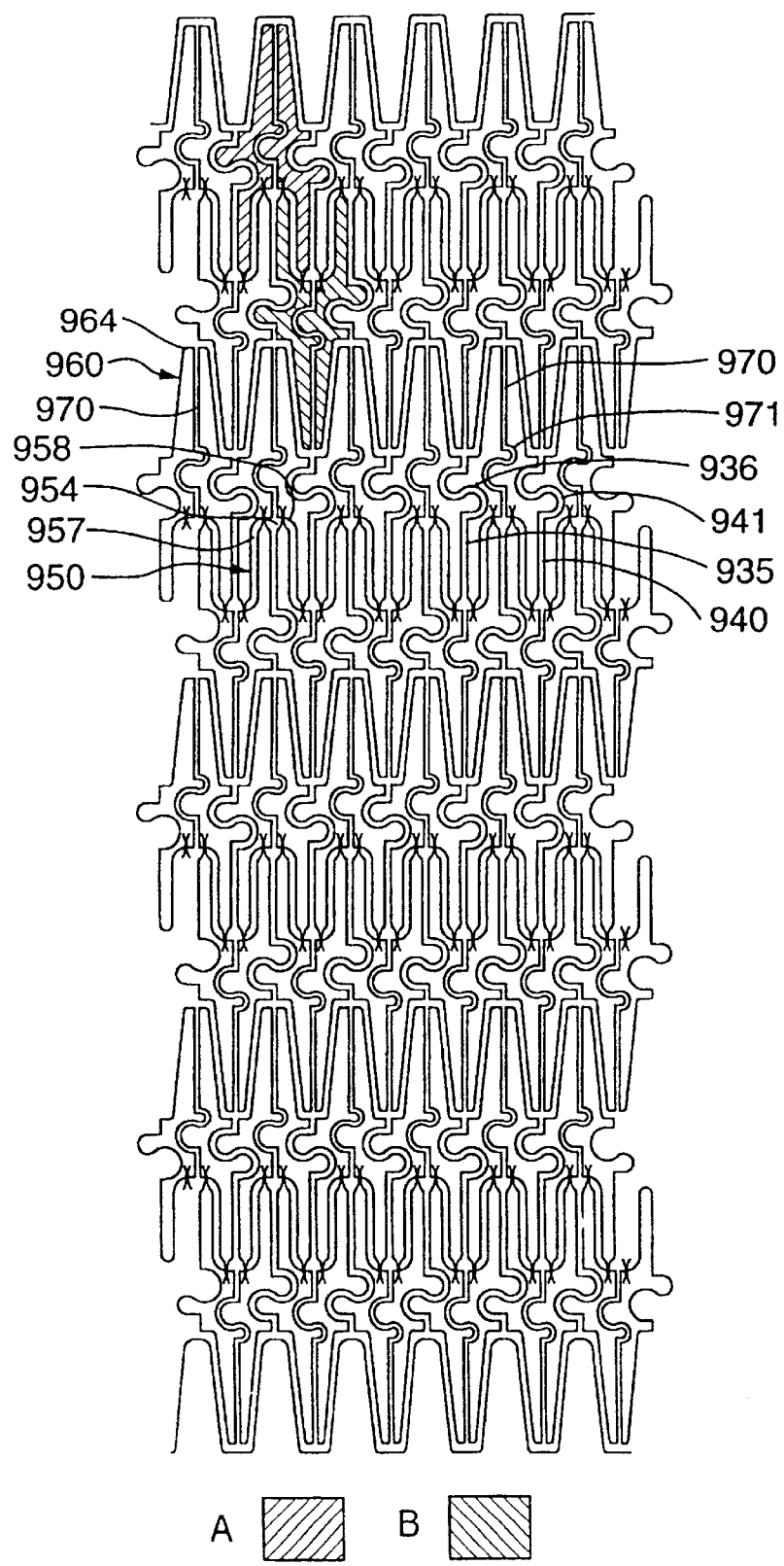

With reference to FIG. 10, repeating pattern A is similar to the one illustrated in FIG. 1. In FIG. 10, concave-shaped wall 950 has been modified to have a flat apex 954 having a pair of rounded shoulders 957,958. Further, a strut 970 has been added to connect flat-apex 954 of concave-shaped wall 950 and segment 964 of convex-shaped wall 960. Further, side walls 935,940 have been modified to include a pair of sinusoidal (or S-shaped) portions 936,941, respectively, adjacent convex-shaped wall 960. Further, strut 970 has been modified to include sinusoidal (or S-shaped) portion 971 adjacent flat apex of concave-shaped wall 950. It should be noted that each sinusoidal (or S-shaped) portion 936,941, 971 in FIG. 10 comprises a pair of adjoined curved sections wherein each curved section has an arc of greater than 180°. Further, the curved sections in sinusoidal (or S-shaped) portions 936,941 are of the same size, whereas the curved sections in sinusoidal (or S-shaped) portion 971 are of different size. A distinct advantage of the interspersion of sinusoidal (or S-shaped) portions 936,941 and sinusoidal (or S-shaped) portion 971 is that substantially uniform radial expansion of all segments in this stent will occur without specific regard to the expansion forces generated by the balloon or other means used to deploy the stent. Further, this design minimizes the force (e.g. pressure from a balloon) required to expand the stent. Still further, this design enhances the lateral flexibility of the stent.

As will be apparent to those of skill in the art, sinusoidal (or S-shaped) portion 971 is offset with respect to sinusoidal (or S-shaped) portions 936,941 in a panel horizontal to the longitudinal axis of repeating pattern A. The offset nature of these sinusoidal (or S-shaped) portions serves to increase the bending points in the stent allowing the stent to bend while avoiding buckling thereof. Thus, the staged distribution of the sinusoidal (or S-shaped) portions over a large portion of the surface area of the stent serves to improve the flexibility of the stent.

The advantages of the various alternate embodiments illustrated in FIGS. 2–10 are discussed hereinabove.

As discussed above, the use of flexure means, such as the sinusoidal (or S-shaped) portions in the design of the stents illustrated in FIGS. 8–10, in the longitudinal struts in the stent design provides the added benefit of improved flexibility of the stent in the unexpanded state. Specifically, during flexure of the stent, provision of such a feature allows the inner stent surface adjacent the bend to compress while concurrently allowing the outer stent surface adjacent the bend to extend, all while maintain substantially intact the integral strength of stent and avoiding buckling of the stent.

Accordingly the provision of such flexure means in the longitudinal struts of an otherwise general stent design is another feature of invention. With reference to FIGS. 12a–12i there are illustrated various alternatives of bowed lateral sections which can be used in place of sinusoidal (or S-shaped) portions 736,741,771 in FIG. 8, sinusoidal (or S-shaped) portions 836,841 in FIG. 9 and sinusoidal (or S-shaped) portions 936,941,971 in FIG. 10. Thus, the flexure means illustrated in FIG. 12a may be considered to be an asymmetric zig-zag whereas that illustrated in FIG. 12b may be considered to be a symmetric zig-zag and that illustrated in FIG. 12c may be considered to be an in line symmetric double peak. The flexure means illustrated in FIG. 12d may be considered to be a single omega, whereas that illustrated in FIG. 12e may be considered to be an inline (and unlinked) double omega and that illustrated in FIG. 12f may be considered to be an opposed (and unlinked) double omega. The flexure means illustrated in FIG. 12g may be considered to be an opposed omega (facilitates extension)/U-joint (facilitates compression). Still further the flexure means illustrated in FIG. 12h may be considered to be a rail flex whereas that illustrated in FIG. 12i may be considered to be an opposed rail flex. Other specific designs which are with the spirit and scope of the present invention will be apparent to those of skill in the art.

Those of skill in the art will recognize that it is possible to combine various of the alternate embodiments illustrated in FIGS. 2–10 and 12 to derive further designs which are still within the spirit and scope of the present invention. Specifically, a preferred embodiment of the present invention involves combining various of the repeating patterns illustrated in FIGS. 2–10 to achieve a stent with relatively flexible and rigid regions, for example, as follows:

F-R
F-R-F
R-F-R wherein F is a relatively flexible region and R is a relatively rigid region. With reference to the embodiments illustrated in FIGS. 1–10, the trackability of the stent through a tortuous pathway is enhanced from the design illustrated in FIG. 1 progressively through to the design illustrated in FIG. 10. For example, an embodiment of the invention is a stent comprising a first section incorporating the design of FIG. 10 and a second section incorporating the design of FIG. 9. It is believed that such a multi-sectional design provides a very desirable combination of lateral flexibility (primarily from the design of FIG. 9) with post-expansion radial rigidity (primarily from the design of FIG. 10).

Another technique by which the relative flexibility/rigidity may be varied along the length of the stent involves varying the thickness of the segments making up the polygon discussed hereinabove. Specifically, the thickness of the segments may be varied in the range of from about 0.0015 to about 0.0045 inches, preferably from about 0.0020 to about 0.0040 inches. The lower the thickness in this range, the more flexible the resulting stent design. Conversely, the higher the thickness in this range, the less flexible the resulting stent design. Thus, by judicious selection of segment thickness, the relative flexibility/rigidity of the stent may be varied along its length.

Figure 11:
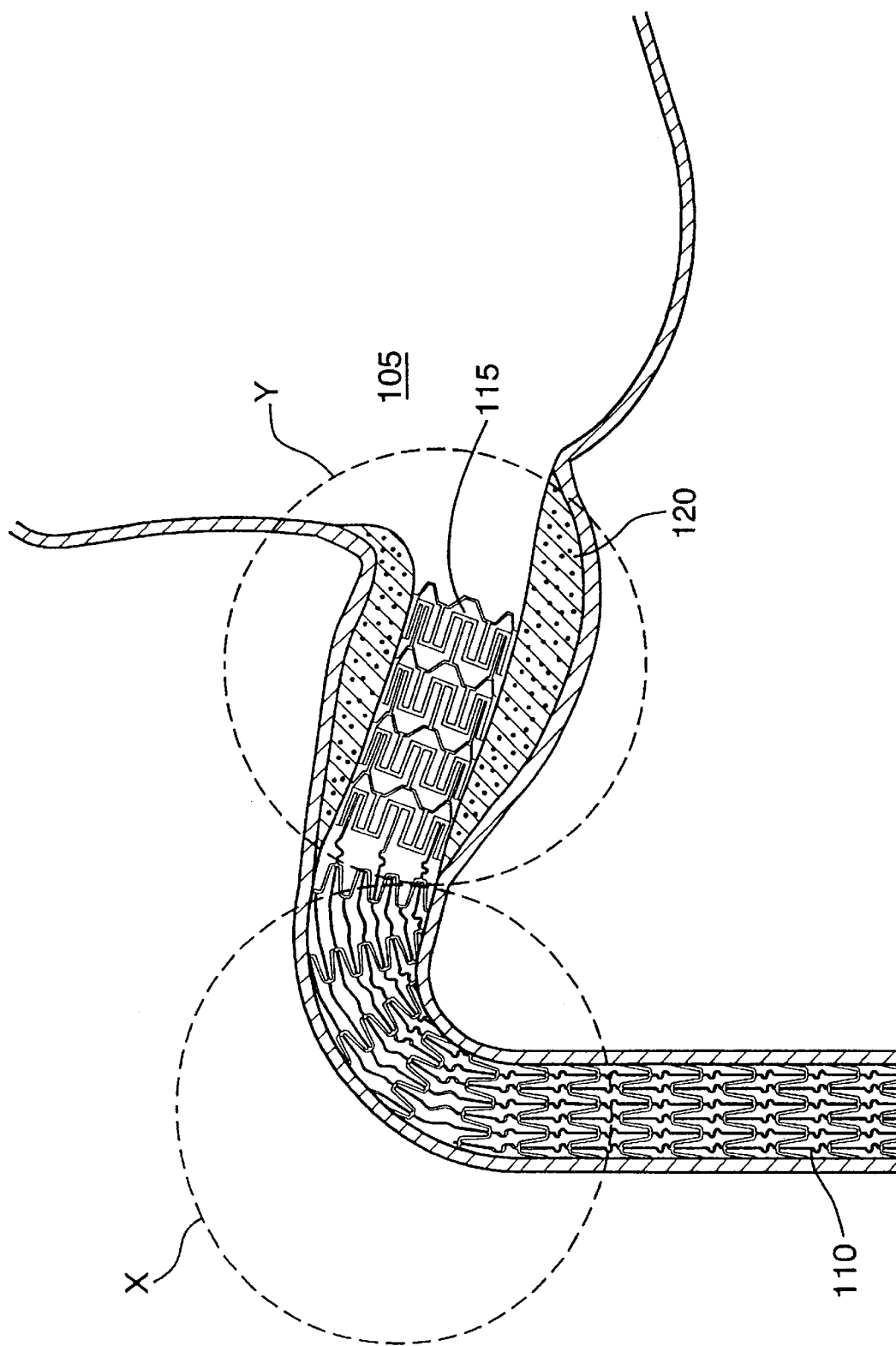
FIG. 11 illustrates an ostial stenosis to which a preferred embodiment of the invention may be applied.
Figure 12A:
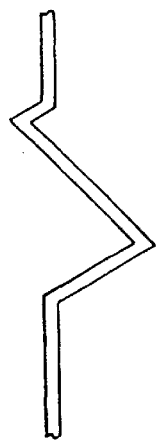
FIGS. 12a–12i illustrate various embodiments of flexure means (in two dimensions) which may be disposed in the longitudinal struts of preferred embodiments of the present stent.
Figure 12B:
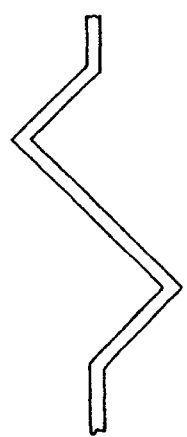
Figure 12D:
Figure 12C:
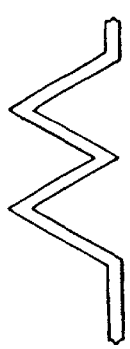
Figure 12E:
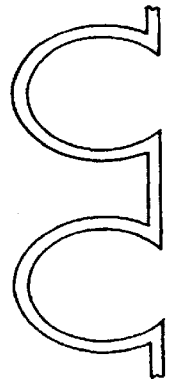
Figure 12F:
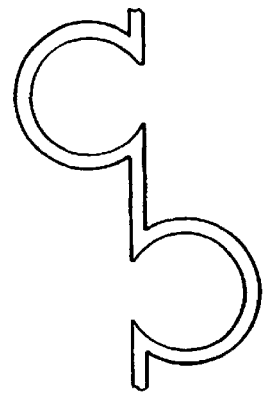
Figure 12G:
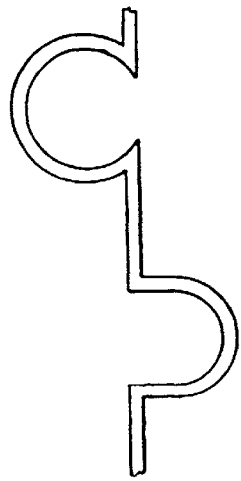
Figure 12H:
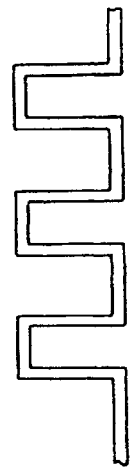
Figure 12I:
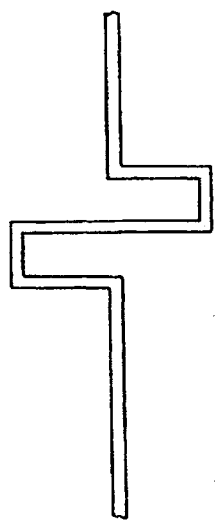

The provision of a stent with a variable relative flexibility/rigidity along its length is believed to be novel, especially a stent comprising a single relatively flexible portion and a single relatively rigid portion (i.e. the F-R embodiment discussed above). Such a stent would find immediate use in a number of applications. For, example, such a stent would very desirable for implantation in an ostial stenosis (these typically occur in coronary arteries, vein grafts and renal arteries). In this regard, an ostial stenosis is illustrated in FIG. 11 thereof. Thus, there is illustrated a right coronary cusp 105, a right coronary artery 110 and an ostial segment 115 of right coronary artery 110. As further illustrated a stenosis 120 presents a narrowing of ostial segment 115. Ideally, a stent capable of implantation into such an ostial stenosis must be of sufficient rigidity after expansion to resist the elastic recoil of the ostial blockage (Region Y in FIG. 11). However, a stent of such sufficient rigidity will be deficient since it will either: (i) be retarded in its advance along the artery due to the sharp bend in the right coronary artery (Region X in FIG. 11); or (ii) traverse the sharp bend in the right coronary artery but subsequently straighten Region X of right coronary artery 110 thereby increasing the likelihood of tearing the artery. Conversely, a stent of sufficiently flexibility to traverse the sharp bend in the right coronary artery (Region X in FIG. 11) is susceptible to recoil in the ostial right coronary artery (Region Y in FIG. 11). Accordingly, to the knowledge of the Applicant, there is no known effective manner by which a stent may be used to treat an ostial stenosis of the type illustrated in FIG. 11. It is believed that a stent having variable relative rigidity/flexibility along its length as discussed above is a novel means by which an ostial stenosis may be treated. FIG. 11 also serves to illustrated the substantially complementary extension and compression of longitudinal members in Region X of the right coronary artery.

The manner by which the present stent is manufactured is not particularly restricted. Preferably, the stent is produced by laser cutting techniques applied to a tubular starting material. Thus, the starting material could be a thin tube of a metal or alloy (non-limiting examples include stainless steel, titanium, tantalum, nitinol, Elgiloy, NP35N and mixtures thereof) which would then have sections thereof cut out to leave repeating pattern A discussed above. Thus, the preferred design of the present stent is one of a tubular wall which is distinct from prior art wire mesh designs wherein wire is conformed to the desired shape and welded in place.

The preferred tubular wall design of the present stent facilitates production and improves quality control by avoiding the use of welds and, instead, utilizing specific cutting techniques.

Preferably, the stent is coated with a solution of 1:2 (mole) copolymer of (methacryloyloxy ethyl)-2-(trimethylanmronium ethyl) phosphate inner salt with lauryl methacrylate in ethanol (as described in Example 2 of International patent application WO-A-93/01221) as follows. The non-expanded stent may be placed in a tube having a slightly larger diameter than the stent. The tube may then be filled with coating solution and the solution allowed to drain steadily from the tube to form a completely coated stent. Immediately thereafter a stream of warm air or nitrogen may be directed through the tube at a linear velocity of 0.1.5 m/s at room temperature to 50° C. for a period of 30 seconds to 5 minutes to dry the coating by evaporation of the ethanol solvent.

As an alternative or in addition (on top or underneath) to this coating, a cross-linkable coating may be used consisting of a polymer of 23 mole % (methacryloyloxy ethyl)-2-(trimethylammonium ethyl) phosphate inner salt, 47 mole % lauryl methacrylate, 5 mole % γtrimethoxysilylpropyl methacrylate and 25 mole % of γhydroxypropyl methacrylate. This may be applied to the sent by the above described technique from a 5 mg/ml ethanoic solution. The solution may be dried as described above and then cured by heating at 70 to 75° C. for a period of at least about 1 hour, for instance overnight. This curing generally results in substantially complete reaction of the methoxy silyl groups, either with other methoxylsily groups or with hydroxy groups derived from the hydroxypropyl methacrylate monomer, driving off methanol. In one preferred embodiment the crosslinkable coating is applied to the cleared stent, cured and then a further coating of the lauryl methacrylate copolymer described above is applied.

The coated stent may be sterilised by ethylene oxide, gamma radiation or electron beam and subsequently mounted onto a balloon catheter for delivery.

Stent 10 can be implanted using a conventional system wherein a guidewire, catheter and balloon can be used to position and expand the stent. Implantation of mono-tubular stents such as stent 10 is conventional and within the purview of a person skilled in the art. See, for example, any one of U.S. Pat. Nos. 4,733,665, 4,739,762, 5,035,706, 5,037,392, 5,102,417, 5,147,385, 5,282,824, 5,316,023 and any of the references cited therein or any of the references cited hereinabove. When the present stent is constructed as a bifurcated stent, it may be implanted using the procedure outlined in the '997 patent application incorporated herein by reference. Such a bifurcated stent may be manufactured, inter alia, by any of the methods disclosed in the Canadian patent application number 2,175,720 filed in Applicant's name on May 3, 1996, the contents of which are hereby incorporated by reference.

It will be apparent to those of skill in the art that implantation of stent 10 can be accomplished by various other means. For example, it is contemplated that the stent can be made of a suitable material which will expand when a certain temperature is reached. In this embodiment, the material may be a metal alloy (e.g. nitinol) capable of self-expansion at a temperature of at least about 30° C., preferably in the range of from about 30° to about 40° C. In this embodiment, the stent could be implanted using a conventional catheter and the radially outward force exerted on the stent would be generated within the stent itself. Further, stent 10 can be designed to expand upon the application of mechanical forces other than those applied by a balloon/catheter. For example, it is possible to implant stent 10 using a catheter equipped with a resisting sleeve or retaining membrane which may then be removed with the catheter once the stent is in position thereby allowing the stent to expand. Thus, in this example, the stent would be resiliently compressed and would self-expanded once the compressive force (i.e. provided by the sleeve or membrane) is removed.

As will be appreciated by those of skill in the art, repeating pattern A has been described hereinabove and illustrated in FIG. 1 in respect of a monotubular stent. Repeating pattern A and all of the features relating thereto illustrated in and described with reference to FIGS. 1–10 (including modification to include the flexure means illustrated in FIGS. 12a–12i) is equally applicable to a bifurcated stent such as the one described and illustrated in the '997 application discussed hereinabove, the contents of which are hereby incorporated by reference.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments.

What is claimed is:

1. A stent comprising:

a plurality of radially-expandable circumferential struts; and a plurality of longitudinal struts, each longitudinal strut having a curved flex member which is spaced apart from any circumferential strut, the curved flex member comprising, in two dimensions, a first curved section and a second curved section;

wherein the first curved section and the second curved section are of a different size.

2. The stent defined in claim 1, wherein the first curved section and the second curved section are on opposite sides of a longitudinal axis of the stent.

3. The stent defined in claim 1, wherein the first curved section comprises a U-shaped section.

4. The stent defined in claim 1, wherein the second curved section comprises a U-shaped section.

5. The stent defined in claim 1, wherein the first curved section and the second curved section each comprise a U-shaped section.

6. The stent defined in claim 5, wherein said first U-shaped section and said second U-shaped section are interconnected.

7. The stent defined in claim 1, further comprising a medicinal coating disposed thereon.

8. A stent system comprising a balloon catheter having an expandable portion, the expandable portion having disposed thereon the stent defined in claim 1.

9. A stent comprising:

a plurality of radially-expandable circumferential struts; and a plurality of longitudinal struts, each longitudinal strut having a curved flex member which is spaced apart from any circumferential strut, the curved flex member comprising a first curved section and a second curved section;

wherein the first curved section and the second curved section are of a different size, wherein the first curved section and the second curved section each comprise a U-shaped section, and wherein said first U-shaped section and said second U-shaped section comprise a pair of straight sections which are: (i) parallel to each other, and (ii) substantially orthogonal to a longitudinal axis of the stent.

10. A stent comprising:

a plurality of radially-expandable circumferential struts; and a plurality of longitudinal struts, each longitudinal strut having a curved flex member which is spaced apart from any circumferential strut, the curved flex member comprising, in two dimensions, a first curved section and a second curved section;

wherein the first curved section and the second curved section are of a different size, at least one of the plurality of radially-expandable circumferential struts having a thickness thereof which varies in the range of from about 0.0015 to about 0.0045 inches.

11. A stent comprising:

a plurality of radially-expandable circumferential struts; and a plurality of longitudinal struts, each longitudinal strut having a curved flex member which is spaced apart from any circumferential strut, the curved flex member comprising, in two dimensions, a first curved section having arc of greater than 180°.

12. The stent defined in claim 11, wherein said curved flex member comprises a second curved section having an arc of greater than 180°.

13. The stent defined in claim 12, wherein the first curved section and the second curved section are on opposite sides of a longitudinal axis of the stent.

14. The stent defined in claim 12, wherein the first curved section and the second curved section have substantially the same shape.

15. The stent defined in claim 12, wherein the first curved section and the second curved section have substantially the same size.

16. The stent defined in claim 12, wherein the first curved section and the second curved have substantially the same size and the same shape.

17. The stent defined in claim 12, wherein the first curved section and the second curved section are interconnected.

18. The stent defined in claim 11, further comprising a medicinal coating disposed thereon.

19. A stent system comprising a balloon catheter having an expandable portion, the expandable portion having disposed thereon the stent defined in claim 11.

20. A stent comprising:

a plurality of radially-expandable circumferential struts; and a plurality of longitudinal struts, each longitudinal strut having a curved flex member which is spaced apart from any circumferential strut, the curved flex member comprising, in two dimensions, a first curved section having arc of greater than 180°, at least one of the plurality of radially-expandable circumferential struts having a thickness thereof which varies in the range of from about 0.0015 to about 0.0045 inches.

21. The stent defined in claim 20, wherein said plurality of radially-expandable circumferential struts and said plurality of longitudinal struts are formed in a porous tubular wall.

22. The stent defined in claim 20, wherein said plurality of longitudinal struts comprises plural flex members disposed in at least one row of longitudinal struts.

* * * * *

UNITED STATES PATENT AND TRADEMARK OFFICE
CERTIFICATE OF CORRECTION

PATENT NO. : 6,758,860 B1
DATED : July 6, 2004
INVENTOR(S) : Ian M. Penn et al.

It is certified that error appears in the above-identified patent and that said Letters Patent is hereby corrected as shown below:

Title page,
Item [73], Assignee, "Envysio Medical Devices ULC (CA)" should read -- Evysio Medical Devices ULC (CA) --.

Signed and Sealed this

Ninth Day of November, 2004

JON W. DUDAS
*Director of the United States Patent and Trademark Office*